United States Patent [19]
Pourcho

[11] Patent Number: 5,158,451
[45] Date of Patent: Oct. 27, 1992

[54] ORTHODONTIC APPLIANCE

[76] Inventor: William S. Pourcho, 751 Chestnut St., Birmingham, Mich. 48008

[21] Appl. No.: 504,644

[22] Filed: Apr. 3, 1990

[51] Int. Cl.⁵ .............................................. A61C 3/00
[52] U.S. Cl. ......................................................... 433/5
[58] Field of Search ........................................... 433/5

[56] References Cited

U.S. PATENT DOCUMENTS

| | | | |
|---|---|---|---|
| 3,401,457 | 9/1968 | Hickham | 433/5 |
| 3,423,832 | 1/1969 | Nelson | 433/5 |
| 4,121,341 | 10/1978 | DeWoskin | 433/5 |
| 4,259,065 | 3/1981 | DeWoskin | 433/5 |
| 4,375,962 | 3/1983 | DeWoskin | 433/5 |
| 4,577,627 | 3/1986 | Garcia | 433/5 |
| 4,600,382 | 7/1986 | Forster | 433/5 |
| 4,988,291 | 1/1991 | Grummons | 433/5 |

FOREIGN PATENT DOCUMENTS 0462159  1/1950  Canada ..................... 433/5

*Primary Examiner*—John J. Wilson
*Attorney, Agent, or Firm*—Gifford, Groh, Sprinkle, Patmore and Anderson

[57] ABSTRACT

An orthodontic appliance for applying an anterior traction to a jaw of a patient is disclosed. The appliance includes a strap assembly which is secured against movement to the upper portion of the patient's head. A pair of side pieces are secured to and depend downwardly from opposite sides of the strap so that a lower end of each side piece is positioned adjacent a cheek of the patient. A U-shaped bar is secured to the lower portions of the side pieces so that the bar extends in front of the patient's mouth. Resilient members, such as rubber bands, that extend between the U-shaped bar and the patient's jaw to impose an anterior traction on the patient's jaw. The anterior force imposed on a patient's jaw is offset by an equal and opposite posterior force transmitted solely to the upper portion of the patient's head through the bar, side pieces and the strap assembly.

8 Claims, 2 Drawing Sheets

ORTHODONTIC APPLIANCE

BACKGROUND OF THE INVENTION

I. Field of the Invention

The present invention relates generally to orthodontic appliances and, more particularly, to an orthodontic appliance for imposing an anterior traction of force on the patient's jaw.

II. Description of the Prior Art

In the practice of orthodontics, it is frequently necessary to move the patient's jaw anteriorly with respect to the patient's head in order to obtain a correct bite. This is especially true with the lower jaw of the patient.

There are a number of previously known appliances with are designed to move the patient's jaw forwardly by imposing anterior force on the patient's jaw. All of these previously known devices generally comprise a head gear or head assembly of one sort which is mounted to the patient's head so that a portion of the head gear is positioned in front of the patient's mouth. Thereafter, elastic members, typically rubber bands, extend between the appliance and the patient's jaw under tension in order to exert the anterior force on the patient's jaw.

As is well known in physics, for each force or reaction there must be an equal and opposite force or reaction. Consequently, in order to impose an anterior force on the patient's jaw, there must be an equal and opposite posterior force also imposed upon the patient.

Many of these previously known devices have thus used pads which engage either the cheekbone area or the chin of the patient. Consequently, when rubber bands are tensioned between the previously known orthodontic device and the patient's jaw, a posterior force is imposed by the appliance against either the patient's cheekbone area, the patient's chin, or both. The rearward or posterior force imposed upon the cheekbone or chin is opposite to and offsets the anterior force imposed on the patient's jaw.

However, both the chin as well as the cheekbones are interconnected with the patient's upper and lower jaws. Consequently, by imposing a posterior force on the cheekbones and/or the patient's chin, these previously known orthodontic appliances disadvantageously counteract the desired anterior force on the patient's jaw. Furthermore, in some cases, the posterior force imposed on the patient's chin and/or cheekbones result in some depression of the cheekbones and/or chin which detracts from the overall facial appearance of the patient.

SUMMARY OF THE PRESENT INVENTION

The present invention provides orthodontic appliance for applying an anterior traction to the jaw of the patient which overcomes all of the previously known disadvantages of the previously known devices.

In brief, the orthodontic appliance of the present invention comprises a strap assembly which is secured to the upper portion of the patient s head against movement. Preferably the strap assembly is constructed of a non-elastic material which encircles the patient's forehead and extends under the rear cranial bulge of the patient's head. Upon tightening the free ends of the strap together beneath the rear cranial bulge of the patient's head, relative movement of the strap with respect to the patient's head is precluded.

A pair of side pieces are then secured to and depend downwardly from opposites of the strap assembly. Consequently, the lower end of each side piece is positioned adjacent one cheek of the patient.

Thereafter, a generally U-shaped bar is secured between the lower ends of the side pieces so that a midportion of the U-shaped bar is positioned in front of the patient 's mouth. Resilient means, such as rubber bands, are then interconnected between the midportion of the bar and the patient's jaw.

With the elastic members under tension, an anterior force is imposed upon the patient's jaw. Simultaneously, the anterior force is offset by a posterior force which is transmitted solely to the upper portion of the patient's head through the bar, side pieces, and the strap assembly.

The present invention further includes means for adjusting both the angular position of the bar with respect to the side pieces, as well as the spacing between the midportion of the bar and the patient's mouth.

BRIEF DESCRIPTION OF THE DRAWING

A better understanding of the present invention will be had upon reference to the following detailed description when read in conjunction with the accompanied drawing, wherein like referenced characters refer to like parts throughout the several views, in English.

DETAILED DESCRIPTION OF A PREFERRED EMBODIMENT OF THE PRESENT INVENTION

Figure 1:
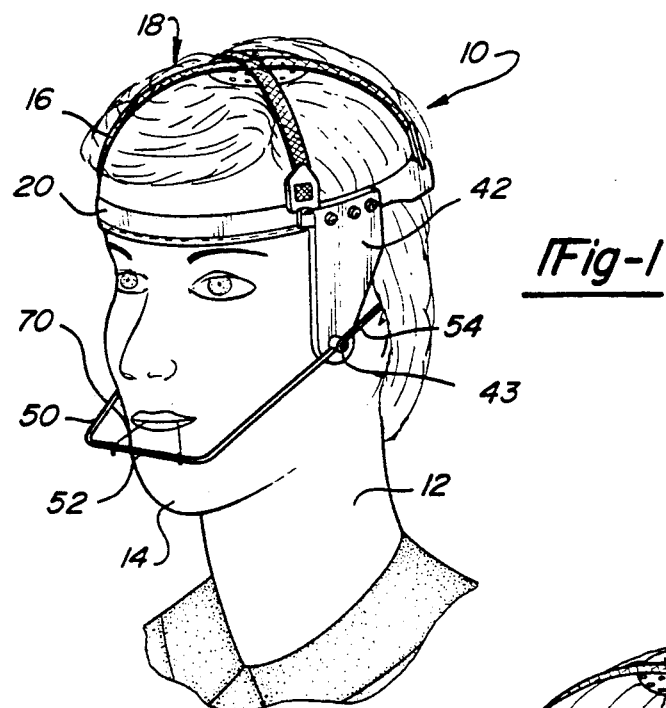
FIG. 1 is a front elevational view illustrating the preferred embodiment of the present invention.
Figure 2:
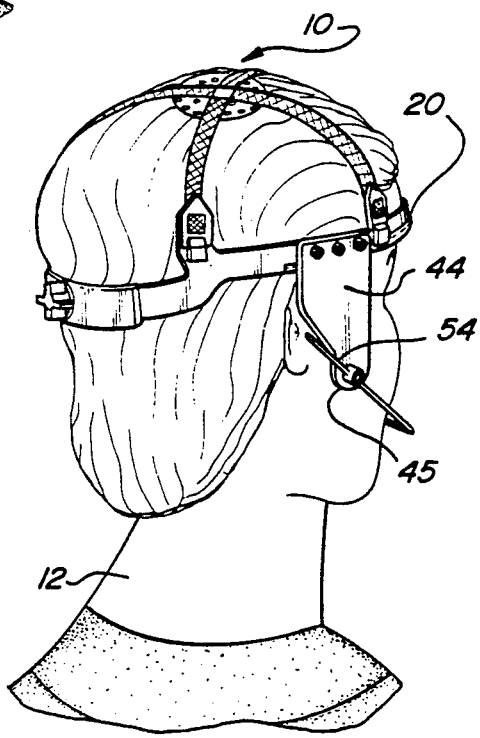
FIG. 2 is a rear view illustrating the preferred embodiment of the present invention.
Figure 3:
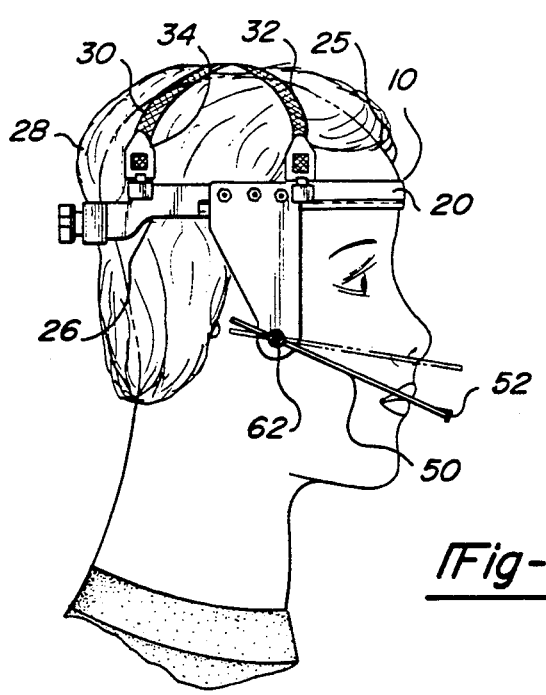
FIG. 3 is a side view illustrating the preferred embodiment of the present invention.

With reference first to the FIGS. 1-3, a preferred embodiment of the orthodontic appliance 10 of the present invention is thereshown for use with a human patient 12. As it will be hereinafter described in greater detail, the orthodontic appliance 10 imposes an anterior traction force on the jaw 14 of the patient 12 and offsets this anterior traction force with a posterior force imposed on the upper portion 16 of the patient's head 18.

Figure 4:
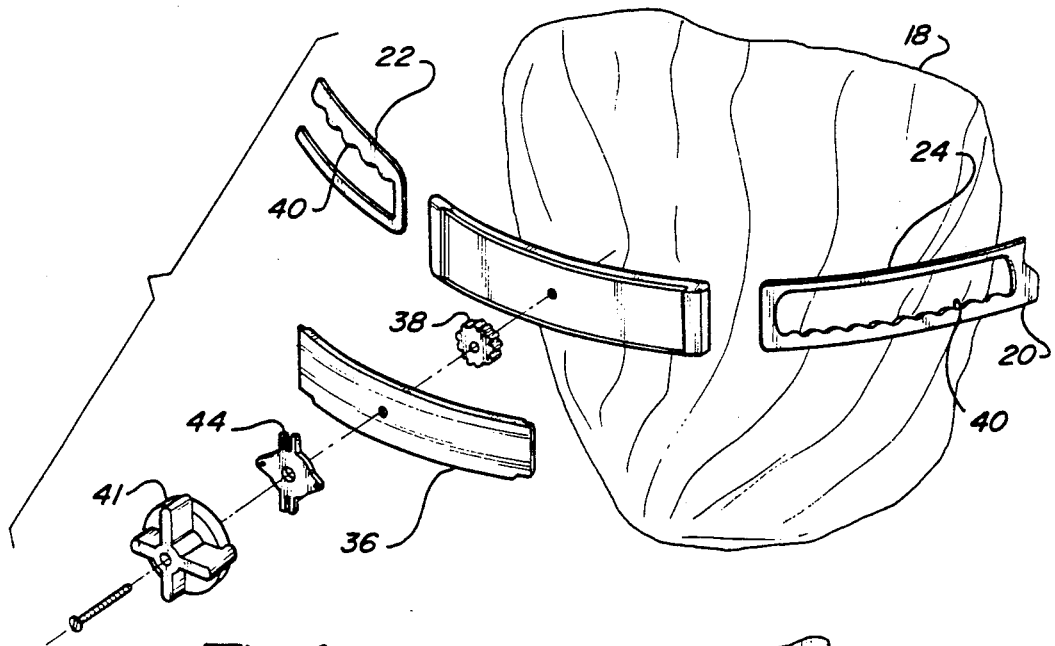
FIG. 4 is an exploded view illustrating a portion of the preferred embodiment of the present invention.

Referring now to FIGS. 1-4, the orthodontic device of the present invention comprises an elongated strap 20 with two free ends 22 and 24 (FIG. 4). The strap 20 is constructed of a non-elastic material, such as nylon or other synthetic material, and extends around the patient's forehead 25 (FIG. 3) so that the two free ends 22 and 24 are positioned in back of the patient's head 18. Furthermore, as best shown in FIG. 3, the strap 20 includes a downward offset portion 26 so that the free ends 22 and 24 of the strap 20 are positioned beneath the rear cranial bulge 28 (FIG. 3) of the patient's head 18.

Referring now to FIGS. 3 and 4, with the strap 20 position around the patient's forehead 25 and behind the rear cranial bulge 28, a pair of cross straps 30 and 32 extend over the top of the patient's head and are secured to the strap 20 to prevent the strap 20 from falling downwardly on the patient's head. These cross straps 30 and 32 preferably have adjustment numbers 34 to adjust their length in order to accommodate patients having different size heads.

As best in FIG. 4, a rachet assembly 36 is provided for securing the free end 22 and 24 of the strap together tightly and securely around the patient's head 18. Although the rachet assembly 36 can be of any conventional construction, preferably a pawl 38 engages cogs 40 formed in the ends 22 and 24 of the strap 20. Consequently, rotation of the pawl 38 by a knob 41 tightens or loosens the strap 20 around the patient's head, depending upon the direction of rotation. A locking member 44 holds the pawl 38 at its adjusted rotational position and thus secures a strap 20 against movement on the patient's head.

With reference FIGS. 1 and 2, a pair of side pieces 42 and 44 are secured to and depend downwardly from opposite sides of the strap 20 so that one side piece 42 has a lower end 43 adjacent the left cheek of the patient 12. Similarly, the other side piece 44 is secured and depends downwardly from the headband 20 so that its lower end 45 is positioned adjacent the right cheek of the patient 12. Both side pieces 42 and 44 are, furthermore, constructed of a rigid material.

Still referring to FIGS. 1 and 2, a generally U-shaped bar 50 has its free end secured to the lower ends 43 and 45 of the side pieces 42 and 44, respectively. In doing so, a midportion 52 (FIG. 1) of the bar 50 is positioned in front of the patient's mouth.

Figure 5:
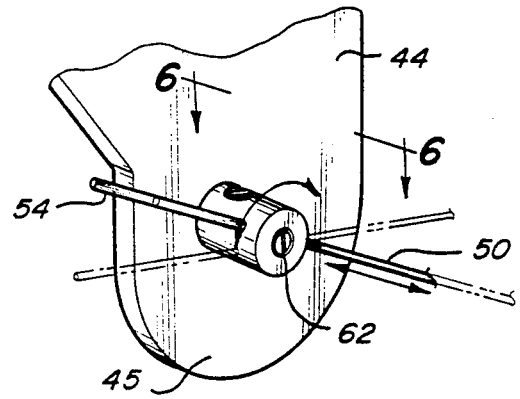
FIG. 5 is a fragmentary diagrametic view of a portion of the preferred embodiment of the present invention and enlarged for clarity.
Figure 6:
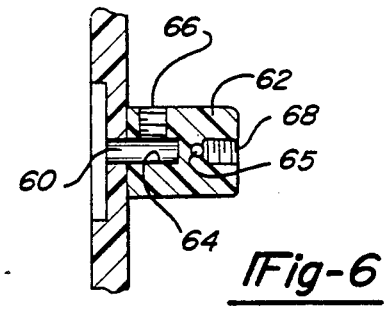
FIG. 6 is a fragmentary sectional view taken substantially along line 6—6 in FIG. 5.

With reference now to FIGS. 5 and 6, although any conventional means, can be used to secure the free ends 54 of the bar 50 to the side piece 44, in the preferred embodiment, the side piece 44 includes an outwardly extending stem 60 (FIG. 6) which protrudes laterally outwardly from the side piece 44. A cylindrical boss 62 having an axial recess 64 is in position over the stem 60 so that the stem 60 nests within the recess 64. A set screw 66 then secures the boss 62 against rotation with respect to the stem 60. Consequently, as best shown in FIG. 5, the position of the boss 62 can be pivoted as shown in phantom line with respect to the side piece 44 and, when pivoted adjusted, locked in place by the set screw 66. The purpose of this pivotal adjustment will be subsequently described.

Still referring to FIGS. 5 and 6, the boss 62 further includes a diametric through bore 65 which slidely receives the free end 54 of the bar 50 therethrough. When the bar 50 is slid to the desired longitudinal position with the respect to the boss 62, a set screw 68 threadly mounted in the boss 62 is tightened so that it abuts against the bar 50 thereby locking the bar 50 to the boss 62. The longitudinal adjustment of the bar 50 with respect to the boss 62 thus allows the distance between the midportion 52 of the bar 50 in the patient's mouth to be adjusted for a purpose to be subsequently described.

In operation, the strap assembly is positioned on the patient's head so that the cross straps 34 and 32 abut against the top of the patient's head while the strap 20 extends around the patient's forehead and behind the rear cranial bulge 28 of the patient's head. Thereafter, the knob 41 is tightened thus pulling the ends 22 and 24 (FIG. 4) of the strap 20 together thereby tightening the strap around the patient's head and under the rear cranial bulge 28 of the patient's head. The strap 20 is tightened so that movement between the strap 20 and the patient's head is prevented.

Thereafter, as best shown in FIG. 3, both the longitudinal position of the bar 50 as well as the angular position (illustrated in FIG. 5) are adjusted and then secured in positioned by the set screws 66 and 68 (FIG. 6). Elastic members 70 (FIG. 1) such as rubber bands are then connected under tension between braces on the patient's teeth and the midportion 52 of the bar 50.

With the elastic members in a state of tension, the elastic members 70 impose an anterior force or traction on the patient's jaw in the desired fashion. This anterior force of traction is offset by an equal and opposite posterior force transmitted solely to the upper portion of the patient's head. This posterior force is transmitted through the bar 50, side piece 42, and strap 20.

The longitudinal adjustment between the bar 50 and the boss 62 allows the distance between the midportion 52 of the bar 50 in the patient's mouth to be adjusted. It, in turn, varies the magnitude of the anterior force imposed by the same elastic members. In other words, a greater force can be exerted using the same elastic members 70 by spacing the midportion 52 of the bar 50, more forwardly, from the patient's mouth and vice versa.

Conversely, by varying the angular adjustment as shown in phantom line in FIG. 3 between the bar 50 and the side piece 42, it is possible to exert not only an anterior force on the patient's jaw, but also a rotary force on the patient's jaw. For example, as shown in FIG. 3, with the bar adjusted to the position in phantom line and the elastic members coupled between the bar 50 and the patient's jaw, a counter clockwise force is exerted upon the patient's jaw.

Another application of this invention is to pull the upper jaw superiorly to eliminate excess bone between the bottom of the nose and the upper incisors. To achieve this superiorly directed force, two straps on either side of the head are attached to an intra-oral wire metal face bow with rubber bands. This intra-oral metal wire face bow is then exerting an upward force with the reciprocal force being applied to the top of the head.

From the foregoing, it can be seen that the present invention provides an orthodontic appliance for imposing an anterior force on the jaw of a patient which is not only simple in construction, but also effective in use. Having described my invention, however, many modifications thereto will become apparent to those skilled in the art to which it pertains without deviation from the spirit of the invention as defined by the scope of the appended claims.

I claim:

1. An orthodontic appliance for applying an anterior traction to a jaw of a patient, said patient having a head, two cheeks, said orthodontic appliance comprising:

a strap assembly, means for securing said strap assembly against movement solely to an upper portion of the patient's head, a pair of rigid side pieces and means for rigidly securing said side pieces against opposite sides of said strap assembly so that said side pieces depend downwardly from said strap assembly and so that a lower end of each side piece is positioned adjacent to but spaced from one cheek of the patient wherein a posterior force applied to said side pieces is transmitted solely to the upper portion of the patient's head, a generally U-shaped bar, means for attaching opposite ends of said bar to said side pieces so that a midportion of said bar is positioned in front of the mouth of the patient, resilient means extending between said midportion of said bar and the jaw of the patient to impose an anterior force on the jaw of the patient, said anterior force being offset by a posterior force transmitted solely to said upper portion of the patient's head through said bar, said side pieces and said strap assembly.

2. The invention as defined in claim 1 wherein said strap assembly comprises:
   an elongated strap constructed of a non-elastic material, said strap extending around the forehead of the patient and having two free ends positioned under a rear cranial bulge of the patient's head, and
   means for connecting and tensioning the free ends of the strap together.

3. The invention as defined in claim 1 wherein said means for attaching said ends of said bar to said side pieces comprises:
   a bore formed in each side piece, said bore being dimensioned to variably slidably receive one end of said bar therethrough, and
   means for locking said end of said bar to said side piece at a longitudinally adjusted position,
   whereby the distance between said midportion of said bar and the patient's jaw can be varied to thereby vary the anterior traction force on the patient's jaw.

4. The invention as defined in claim 3 wherein said locking means comprises a set screw which threadably engages said side piece and abuts against said bar.

5. The invention as defined in claim 1 and comprising means for varying the angle between said side pieces and said bar.

6. The invention as defined in claim 5 wherein said angle varying means comprises a boss, means for pivotally mounting said boss to said side piece, means for locking said boss to said side piece at an adjusted pivotal position, said bar being secured to said boss.

7. The invention as defined in claim 6 wherein said locking means comprises a set screw.

8. The invention wherein said strap securing means comprises a ratchet assembly.

* * * * *